United States Patent
Johnson et al.

(10) Patent No.: US 8,962,028 B2
(45) Date of Patent: *Feb. 24, 2015

(54) TOPICAL STEROID COMPOSITION AND METHOD

(71) Applicant: MiCal Pharmaceuticals LLC—H Series, a Series of MiCal Pharmaceuticals LLC, a Multi-Division Limited Liability Company

(72) Inventors: Keith A. Johnson, Durham, NC (US); Karl F. Popp, Schodack Landing, NY (US)

(73) Assignee: MiCal Pharmaceuticals LLC—H Series, a Series of MiCal Pharmaceuticals LLC, a Multi-Division Limited Liability Company, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/921,833

(22) Filed: Jun. 19, 2013

(65) Prior Publication Data

US 2014/0112991 A1 Apr. 24, 2014

Related U.S. Application Data

(60) Provisional application No. 61/715,467, filed on Oct. 18, 2012.

(51) Int. Cl.
*A61K 47/00* (2006.01)
*C07J 5/00* (2006.01)
(Continued)

(52) U.S. Cl.
CPC .............. *A61K 47/44* (2013.01); *A61K 47/10* (2013.01); *A61K 47/14* (2013.01); *A61K 47/12* (2013.01); *A61K 9/0014* (2013.01); *A61K 47/08* (2013.01); *A61K 9/06* (2013.01); *A61Q 19/00* (2013.01)

USPC .......................... 424/489; 514/171; 514/180

(58) Field of Classification Search
None
See application file for complete search history.

(56) References Cited

U.S. PATENT DOCUMENTS 4,619,921 A 10/1986 Kalvoda et al.
4,918,065 A * 4/1990 Stindl et al. .................. 514/179
(Continued)

FOREIGN PATENT DOCUMENTS

WO WO 2006110534 A2 * 10/2006

OTHER PUBLICATIONS

Xunquan, L. et al., Treatment of Localized Vitiligo with Ulobetasol Cream, *International Journal of Dermatology*, 29(4): 295-7, May 1990.

(Continued)

*Primary Examiner* — Ernst V Arnold
*Assistant Examiner* — Kyung Sook Chang
(74) *Attorney, Agent, or Firm* — Gifford, Krass, Sprinkle, Anderson & Citkowski, P.C.

(57) ABSTRACT

Storage stable, topical lotion compositions for treating corticosteroid-responsive dermatoses are provided by the present invention which include a halobetasol material comprising halobetasol or its pharmaceutically acceptable salts, esters, and solvates; and a pharmaceutically acceptable carrier which includes: (a) one or more fatty alcohols and/or one or more alkoxylated fatty alcohols, (b) one or more polyol humectants, and (c) diisopropyl adipate. Storage stable, topical lotion compositions for treating corticosteroid-responsive dermatoses are provided by the present invention which include 0.05% halobetasol propionate; and a pharmaceutically acceptable carrier which includes: (a) one or more fatty alcohols and/or one or more alkoxylated fatty alcohols, (b) one or more polyol humectants, and (c) diisopropyl adipate.

29 Claims, 2 Drawing Sheets

(51) Int. Cl.
*A61K 47/44* (2006.01)
*A61K 47/10* (2006.01)
*A61K 47/14* (2006.01)
*A61K 47/12* (2006.01)
*A61K 9/00* (2006.01)
*A61K 47/08* (2006.01)
*A61K 9/06* (2006.01)
*A61Q 19/00* (2006.01)

(56) References Cited

U.S. PATENT DOCUMENTS

| | | | |
|---|---|---|---|
| 5,064,655 A | 11/1991 | Uster et al. | |
| 5,219,877 A | 6/1993 | Shah et al. | |
| 5,326,566 A | 7/1994 | Parab | |
| 5,702,711 A | 12/1997 | Parab | |
| 5,705,168 A | 1/1998 | Parab | |
| 6,315,980 B1 | 11/2001 | Denda et al. | |
| 6,368,687 B1 | 4/2002 | Joseph et al. | |
| 6,387,383 B1 | 5/2002 | Dow et al. | |
| 6,517,847 B2* | 2/2003 | Dow et al. | 424/401 |
| 6,647,058 B1 | 11/2003 | Bremer et al. | |
| 6,656,928 B1 | 12/2003 | McCadden | |
| 6,673,374 B2 | 1/2004 | Murad | |
| 6,756,032 B1 | 6/2004 | Tepper et al. | |
| 6,781,027 B2 | 8/2004 | Fenwick et al. | |
| 6,790,203 B2 | 9/2004 | Een | |
| 6,830,758 B2 | 12/2004 | Nichols et al. | |
| 7,175,837 B2 | 2/2007 | Schiltz | |
| 7,208,485 B2 | 4/2007 | Adin et al. | |
| 7,220,424 B2 | 5/2007 | Gans et al. | |
| 7,682,623 B2 | 3/2010 | Eini et al. | |
| 7,704,518 B2 | 4/2010 | Tamarkin et al. | |
| 7,829,107 B2 | 11/2010 | Popp et al. | |
| 7,888,319 B2 | 2/2011 | Gourdie et al. | |
| 8,016,811 B2 | 9/2011 | Smith et al. | |
| 8,206,721 B2 | 6/2012 | Stutz et al. | |
| 8,809,307 B2* | 8/2014 | Angel et al. | 514/169 |
| 2005/0153946 A1* | 7/2005 | Hirsh et al. | 514/170 |
| 2006/0275218 A1 | 12/2006 | Tamarkin et al. | |
| 2007/0189980 A1 | 8/2007 | Zhang et al. | |
| 2007/0196457 A1 | 8/2007 | Zhang et al. | |
| 2007/0196459 A1 | 8/2007 | Zhang et al. | |
| 2008/0025929 A1 | 1/2008 | Burton et al. | |
| 2009/0018175 A1 | 1/2009 | Kanari et al. | |
| 2010/0240621 A1* | 9/2010 | Sen et al. | 514/170 |
| 2012/0129824 A1 | 5/2012 | Angel et al. | |

OTHER PUBLICATIONS

Non-Final Office Action dated May 14, 2014, U.S. Appl. No. 13/921,859 (22 pages).

* cited by examiner

TOPICAL STEROID COMPOSITION AND METHOD

REFERENCE TO RELATED APPLICATION

This application claims priority to U.S. Provisional Patent Application Ser. No. 61/715,467, filed Oct. 18, 2012, the entire content of which is incorporated herein by reference.

FIELD OF THE INVENTION

This invention relates to topical preparations for the treatment of skin conditions. More particularly the invention relates to a storage stable, lotion based composition of a corticosteroid material such as halobetasol propionate and related species, and to methods for the use of such compositions in the treatment of dermatoses.

BACKGROUND OF THE INVENTION

Halobetasol propionate, is in widespread use for the treatment of various dermatological conditions. Typically, halobetasol materials are used in cream or ointment based preparations, and one such product in wide commercial use is sold under the trade name "Ultravate® Cream" (halobetasol propionate 0.05% cream). Ultravate® Cream is generally regarded as a standard in the art. While, in many instances, physicians and/or patients prefer lotion-based preparations, it is generally believed that lotion-based preparations of corticosteroids are inferior in their therapeutic performance as compared to corresponding cream-based preparations.

As will be explained in detail hereinbelow, the present invention is directed to lotion-based preparations of halobetasol propionate and its salts, as well as other halobetasol esters and their salts, solvates, and the like (collectively "halobetasol materials"). Examples of halobetasol esters include, but are not limited to, acetate and butyrate esters. Halobetasol propionate 0.05% lotion of the present invention has high patient acceptability and demonstrates a clinical efficacy which is equal to, and in many instances superior to, that of cream-based halobetasol propionate 0.05% preparations. In addition, it has been found that the compositions of the present invention are stable and demonstrate very good long term storage stability. As will be further explained herein below, experimental data demonstrates that compositions of the present invention are very effective in reducing transepidermal water loss (TEWL) which is a highly desirable benefit in the management of dry and inflammatory skin conditions. Skin conductance studies have also demonstrated that the compositions of the present invention very rapidly penetrate outer skin layers ensuring optimal hydration. The compositions of the present invention comprise particular combinations of ingredients which interact synergistically to produce the enhanced results described above.

SUMMARY OF THE INVENTION

Storage stable, topical lotion compositions for treating corticosteroid-responsive dermatoses are provided by the present invention which include a halobetasol material comprising halobetasol or its pharmaceutically acceptable salts, esters, and solvates; and a pharmaceutically acceptable carrier which includes: (a) one or more fatty alcohols and/or one or more alkoxylated fatty alcohols, (b) one or more polyol humectants, and (c) diisopropyl adipate.

Optionally, the fatty alcohol included in compositions of the present invention is selected from the group consisting of lauryl alcohol, myristyl alcohol, cetyl alcohol, stearyl alcohol, octyldodecanol, and mixtures thereof.

Optionally, the alkoxylated fatty alcohol is an ethoxylated alcohol selected from the group consisting of lauryl alcohol, myristyl alcohol, cetyl alcohol, stearyl alcohol, octyldodecanol, and mixtures thereof.

Optionally, the polyol humectant is selected from the group consisting of glycerin, propylene glycol, butylene glycol, dipropylene glycol, pentylene glycol, and mixtures thereof.

Storage stable, topical lotion compositions for treating corticosteroid-responsive dermatoses are provided by the present invention which include halobetasol propionate; and a pharmaceutically acceptable carrier which includes: (a) one or more fatty alcohols and/or one or more alkoxylated fatty alcohols, (b) one or more polyol humectants, and (c) diisopropyl adipate.

Storage stable, topical lotion compositions for treating corticosteroid-responsive dermatoses are provided by the present invention which include halobetasol propionate; and a pharmaceutically acceptable carrier which includes: (a) one or more fatty alcohols and/or one or more alkoxylated fatty alcohols, wherein the fatty alcohol is selected from the group consisting of lauryl alcohol, myristyl alcohol, cetyl alcohol, stearyl alcohol, octyldodecanol, and mixtures thereof, (b) one or more polyol humectants, and (c) diisopropyl adipate.

Storage stable, topical lotion compositions for treating corticosteroid-responsive dermatoses are provided by the present invention which include halobetasol propionate; and a pharmaceutically acceptable carrier which includes: (a) one or more fatty alcohols and/or one or more alkoxylated fatty alcohols, wherein the alkoxylated fatty alcohol is an ethoxylated alcohol selected from the group consisting of lauryl alcohol, myristyl alcohol, cetyl alcohol, stearyl alcohol, octyldodecanol, and mixtures thereof, (b) one or more polyol humectants, and (c) diisopropyl adipate.

Storage stable, topical lotion compositions for treating corticosteroid-responsive dermatoses are provided by the present invention which include halobetasol propionate; and a pharmaceutically acceptable carrier which includes: (a) one or more fatty alcohols, wherein the fatty alcohol is selected from the group consisting of lauryl alcohol, myristyl alcohol, cetyl alcohol, stearyl alcohol, octyldodecanol, and mixtures thereof, and/or one or more alkoxylated fatty alcohols, wherein the alkoxylated fatty alcohol is an ethoxylated alcohol selected from the group consisting of lauryl alcohol, myristyl alcohol, cetyl alcohol, stearyl alcohol, octyldodecanol, and mixtures thereof, (b) one or more polyol humectants, and (c) diisopropyl adipate.

Storage stable, topical lotion compositions for treating corticosteroid-responsive dermatoses are provided by the present invention which include halobetasol propionate; and a pharmaceutically acceptable carrier which includes: (a) one or more fatty alcohols and/or one or more alkoxylated fatty alcohols, (b) one or more polyol humectants, wherein the polyol humectant is selected from the group consisting of glycerin, propylene glycol, butylene glycol, dipropylene glycol, pentylene glycol, and mixtures thereof, and (c) diisopropyl adipate.

Storage stable, topical lotion compositions for treating corticosteroid-responsive dermatoses are provided by the present invention which include halobetasol propionate; and a pharmaceutically acceptable carrier which includes: (a) one or more fatty alcohols and/or one or more alkoxylated fatty alcohols, wherein the fatty alcohol is selected from the group consisting of lauryl alcohol, myristyl alcohol, cetyl alcohol, stearyl alcohol, octyldodecanol, and mixtures thereof, (b) one or more polyol humectants, wherein the polyol humectant is selected from the group consisting of glycerin, propylene glycol, butylene glycol, dipropylene glycol, pentylene glycol, and mixtures thereof, and (c) diisopropyl adipate.

Storage stable, topical lotion compositions for treating corticosteroid-responsive dermatoses are provided by the present invention which include halobetasol propionate; and a pharmaceutically acceptable carrier which includes: (a) one or more fatty alcohols and/or one or more alkoxylated fatty alcohols, wherein the alkoxylated fatty alcohol is an ethoxylated alcohol selected from the group consisting of lauryl alcohol, myristyl alcohol, cetyl alcohol, stearyl alcohol, octyldodecanol, and mixtures thereof, (b) one or more polyol humectants, wherein the polyol humectant is selected from the group consisting of glycerin, propylene glycol, butylene glycol, dipropylene glycol, pentylene glycol, and mixtures thereof, and (c) diisopropyl adipate.

Storage stable, topical lotion compositions for treating corticosteroid-responsive dermatoses are provided by the present invention which include halobetasol propionate; and a pharmaceutically acceptable carrier which includes: (a) one or more fatty alcohols, wherein the fatty alcohol is selected from the group consisting of lauryl alcohol, myristyl alcohol, cetyl alcohol, stearyl alcohol, octyldodecanol, and mixtures thereof, and/or one or more alkoxylated fatty alcohols, wherein the alkoxylated fatty alcohol is an ethoxylated alcohol selected from the group consisting of lauryl alcohol, myristyl alcohol, cetyl alcohol, stearyl alcohol, octyldodecanol, and mixtures thereof, (b) one or more polyol humectants, wherein the polyol humectant is selected from the group consisting of glycerin, propylene glycol, butylene glycol, dipropylene glycol, pentylene glycol, and mixtures thereof, and (c) diisopropyl adipate.

Storage stable, topical lotion compositions for treating corticosteroid-responsive dermatoses provided by the present invention which include halobetasol propionate; and a pharmaceutically acceptable carrier which includes: (a) one or more fatty alcohols and/or one or more alkoxylated fatty alcohols, (b) one or more polyol humectants, and (c) diisopropyl adipate, wherein the amount of said halobetasol propionate after storage for six months at 40° C. is >98.5% of the total amount of halobetasol propionate present at the time of manufacture of the topical lotion, wherein the amount of degradation of said halobetasol propionate after storage for 26 months at 30° C. is <1% of the total amount of halobetasol propionate present at the time of manufacture of the topical lotion and wherein the amount of degradation of said halobetasol propionate after storage at 25° C. for 30 months is <3%% of the total amount of halobetasol propionate present at the time of manufacture of the topical lotion.

Storage stable, topical lotion compositions for treating corticosteroid-responsive dermatoses provided by the present invention which include halobetasol propionate; and a pharmaceutically acceptable carrier which includes: (a) one or more fatty alcohols and/or one or more alkoxylated fatty alcohols, (b) one or more polyol humectants, and (c) diisopropyl adipate, wherein the amount of degradation of said halobetasol propionate after storage for six months at 40° C. is <1.5% of the total amount of said halobetasol propionate, wherein the amount of degradation of said halobetasol propionate after storage for 26 months at 30° C. is <1% of said halobetasol propionate and wherein the amount of degradation of said halobetasol propionate after storage at 25° C. for 30 months is <3% of said halobetasol propionate.

Optionally, a topical composition of the present invention further includes a coloring agent, a preservative, a pH control agent, a viscosity control agent, a fragrance; or a combination of any two or more thereof.

Storage stable, topical lotion compositions for treating corticosteroid-responsive dermatoses are provided by the present invention which include halobetasol propionate; and a pharmaceutically acceptable carrier which includes: (a) one or more fatty alcohols and/or one or more alkoxylated fatty alcohols, (b) one or more polyol humectants, and (c) diisopropyl adipate, wherein the ratio of said fatty alcohols and alkoxylated fatty alcohols to said humectants, to said diisopropyl adipate is, on a weight basis, in the range of 30-60:30-60:5-15.

Storage stable, topical lotion compositions for treating corticosteroid-responsive dermatoses are provided by the present invention which include halobetasol propionate; and a pharmaceutically acceptable carrier which includes: (a) one or more fatty alcohols and/or one or more alkoxylated fatty alcohols, (b) one or more polyol humectants, and (c) diisopropyl adipate, wherein the ratio of said fatty alcohols and alkoxylated fatty alcohols to said humectants, to said diisopropyl adipate is, on a weight basis, in the range of 39-48:39-50:10-15.

Storage stable, topical lotion compositions for treating corticosteroid-responsive dermatoses are provided by the present invention which include halobetasol propionate; and a pharmaceutically acceptable carrier which includes: (a) one or more fatty alcohols and/or one or more alkoxylated fatty alcohols, (b) one or more polyol humectants, and (c) diisopropyl adipate, wherein the weight ratio of said fatty alcohols and ethoxylated fatty alcohols to said polyol humectants to said diisopropyl adipate is in the range of 44-46:40-43:11-13.

Storage stable, topical lotion compositions for treating corticosteroid-responsive dermatoses are provided by the present invention which include halobetasol propionate; and a pharmaceutically acceptable carrier which includes: (a) one or more fatty alcohols and/or one or more alkoxylated fatty alcohols, (b) one or more polyol humectants, and (c) diisopropyl adipate, wherein the weight ratio of said fatty alcohols and ethoxylated fatty alcohols to said polyol humectants to said diisopropyl adipate is 46:42:12.

Storage stable, topical lotion compositions for treating corticosteroid-responsive dermatoses are provided by the present invention which include on a weight basis: 0.02-0.10% of a halobetasol material; 1-5% of diisopropyl adipate; 5-15% octyl dodecanol; 0.50-2% of polyethylene glycol 1000 cetyl ether; 0.50-2% of a surfactant such as poloxamer 407; 1-3% cetyl alcohol; 1-2% stearyl alcohol; 0.05-0.2% of a preservative such as a paraben preservative, for example propyl paraben and/or butyl paraben; 5-15% propylene glycol; 1-5% glycerin; an alkali such as sodium hydroxide, potassium hydroxide, or the like in an amount sufficient to adjust the pH of the composition to a range of approximately 5-6.5, and in particular 5.2-6.2; optionally a viscosity control agent which may be a cross-linked polyacrylate such as a carbomer in an amount of 0.1-0.2%; and water q.s.

Storage stable, topical lotion compositions for treating corticosteroid-responsive dermatoses are provided by the present invention which include on a weight basis: 0.05% of a halobetasol material; 3.5% of diisopropyl adipate; 10% octyl dodecanol; 1% of polyethylene glycol 1000 cetyl ether; 1% of a surfactant such as poloxamer 407; 2% cetyl alcohol; 0.66% stearyl alcohol; 0.15% of a preservative such as a paraben preservative, for example propyl paraben and/or butyl paraben; 10% propylene glycol; 2.5% glycerin; an alkali such as sodium hydroxide, potassium hydroxide, or the like in an amount sufficient to adjust the pH of the composition to a range of approximately 5-6.5; optionally a viscosity control agent which may be a cross-linked polyacrylate such as a carbomer in an amount of 0.15%; and water q.s.

Storage stable, topical lotion compositions for treating corticosteroid-responsive dermatoses provided by the present invention which include halobetasol propionate; and a pharmaceutically acceptable carrier which includes: (a) one or more fatty alcohols and/or one or more alkoxylated fatty alcohols, (b) one or more polyol humectants, and (c) diisopropyl adipate, wherein said topical lotion composition is an oil-in-water emulsion of droplets having a mean particle size in the range of 0.1-50 microns and a distribution of particle sizes in the range of 0.1-50 microns.

Storage stable, topical lotion compositions for treating corticosteroid-responsive dermatoses provided by the present invention which include halobetasol propionate; and a pharmaceutically acceptable carrier which includes: (a) one or more fatty alcohols and/or one or more alkoxylated fatty alcohols, (b) one or more polyol humectants, and (c) diisopropyl adipate, wherein said topical lotion composition is an oil-in-water emulsion of droplets having a mean particle size in the range of 1-10 microns and a distribution of particle sizes in the range of 0.15-15 microns.

Storage stable, topical lotion compositions for treating corticosteroid-responsive dermatoses provided by the present invention which include halobetasol propionate; and a pharmaceutically acceptable carrier which includes: (a) one or more fatty alcohols and/or one or more alkoxylated fatty alcohols, (b) one or more polyol humectants, and (c) diisopropyl adipate, wherein said topical lotion composition is an oil-in-water emulsion of droplets having a mean particle size in the range of 1.5-7 microns and a distribution of particle sizes in the range of 0.175-10 microns.

Methods for treating steroid responsive dermatoses are provided by the present invention that include topically administering to a patient in need thereof, a storage stable, topical lotion composition of the present invention. According to aspects of the present invention, said topical lotion composition is packaged in a container suitable for storage and delivery of said composition.

A container suitable for storage and delivery of a storage stable, topical lotion composition of the present invention is optionally comprised of a ferrous alloy, aluminum, glass, plastic, or combinations thereof and further optionally includes one or more protective coatings.

A container suitable for storage and delivery of a storage stable, topical lotion composition of the present invention optionally includes at least two separate compartments wherein said storage stable, topical lotion composition of the present invention is disposed in one of said compartments.

Methods for treating steroid responsive dermatoses are provided by the present invention that include topically administering to a patient in need thereof, a storage stable, topical lotion composition of the present invention and wherein the patient is further instructed to prepare the area to be treated by cleansing with a suitable surfactant-containing composition.

Methods for treating steroid responsive dermatoses are provided by the present invention that include topically administering to a patient in need thereof, a storage stable, topical lotion composition of the present invention wherein said treatment is as effective to reduce transepidermal water loss as a cream formulation, Ultravate® cream, compared to a shaved skin control.

Methods for treating steroid responsive dermatoses are provided by the present invention that include topically administering to a patient in need thereof, a storage stable, topical lotion composition of the present invention wherein said treatment is effective to produce an improvement in skin surface hydration levels as measured with a Skicon-200 conductance apparatus and wherein said improvement is observed at 2 hours post treatment and/or at 4 hours post treatment.

Methods for the preparation of a storage stable, topical lotion composition are provided according to the present invention including the steps of: preparing an aqueous phase that includes a first portion of the components of said topical lotion composition; maintaining said aqueous phase at a temperature in the range of 40-50° C.; preparing an oil phase that includes a second portion of the components of said topical lotion composition; adding said oil phase to said aqueous phase while stirring at a temperature of about 40-50° C. so as to obtain an emulsion; cooling said emulsion to a temperature of about 25-35° C.; and adjusting the pH of said emulsion to a pH in the range of 5.0-6.5, preferably 5.2-6.2.

DETAILED DESCRIPTION OF THE INVENTION

Figure 1:
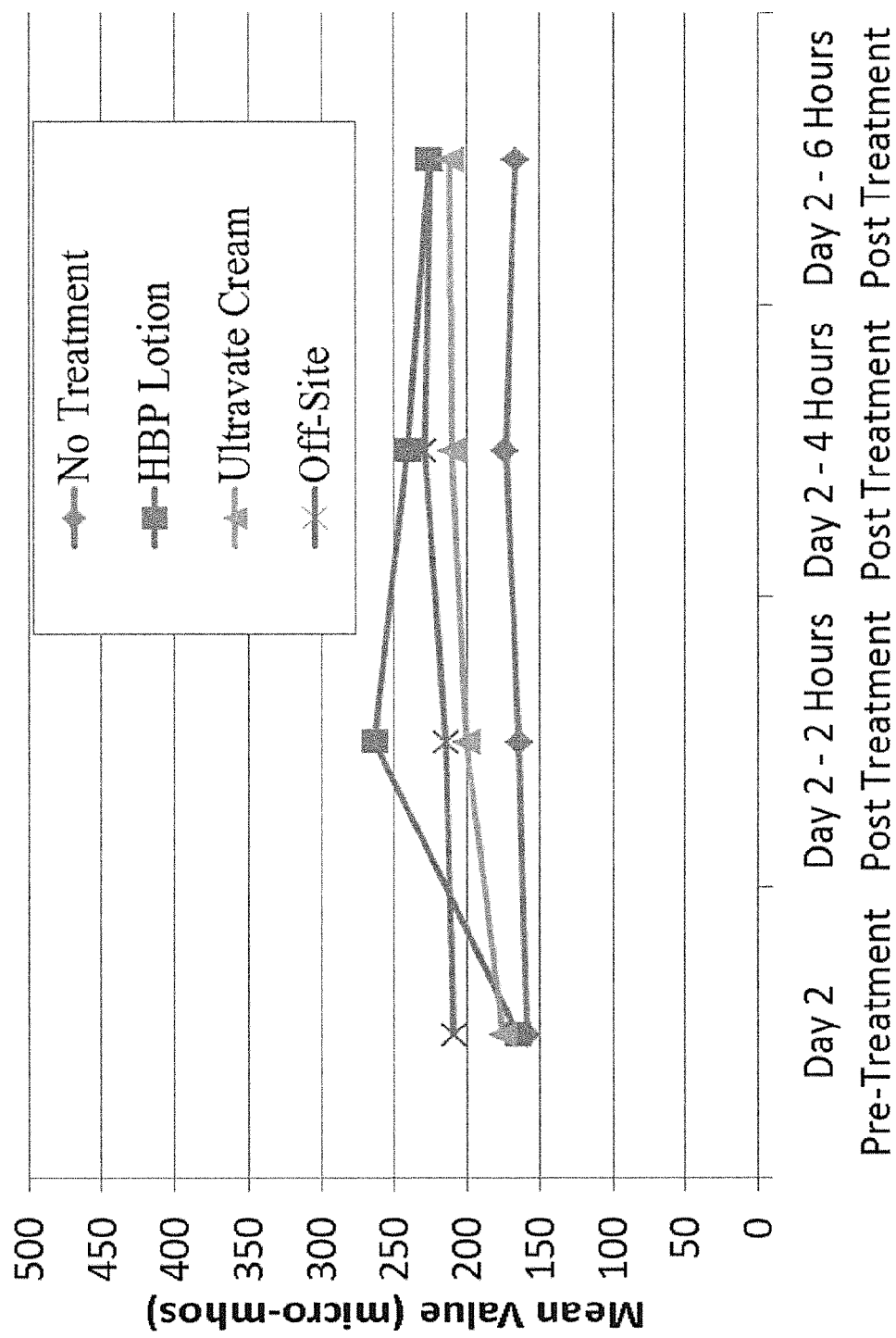
FIG. 1 is a graph showing results of Skicon-200 skin conductance analysis comparing a topical lotion composition of the present invention halobetasol propionate lotion (HBP Lotion) with Ultravate® cream.

The singular terms "a," "an," and "the" as used herein are not intended to be limiting and include plural referents unless explicitly stated otherwise or the context clearly indicates otherwise.

Compositions

Storage stable, topical lotion compositions for treating a steroid-responsive skin disorder or condition are provided by the present invention which include a halobetasol material comprising halobetasol and/or a pharmaceutically acceptable salt, ester, or solvate thereat and a pharmaceutically acceptable carrier which includes: (a) one or more fatty alcohols and/or one or more alkoxylated fatty alcohols, (b) one or more polyol humectants, and (c) diisopropyl adipate.

Storage stable, topical lotion compositions for treating a steroid-responsive skin disorder or condition are provided by the present invention which include a halobetasol material comprising halobetasol propionate; and a pharmaceutically acceptable carrier which includes: (a) one or more fatty alcohols and/or one or more alkoxylated fatty alcohols, (b) one or more polyol humectants, and (c) diisopropyl adipate.

The one or more fatty alcohols and/or one or more alkoxylated fatty alcohols included in compositions of the present invention have a linear or branched carbon backbone that has 6-22 carbon atoms. According to certain aspects of the invention, the one or more fatty alcohols and/or one or more alkoxylated fatty alcohols included in compositions of the present invention have a linear or branched carbon backbone that has 10-18 carbon atoms.

The fatty alcohol may, in some instances, comprise a long chain alcohol such as lauryl alcohol, myristyl alcohol, cetyl alcohol, stearyl alcohol, and octyldodecanol, used either singly or in combination. Yet other fatty alcohols will be apparent to those of skill in the art.

In the preparations of the present invention, the compositions may further include alkoxylated forms of the fatty alcohols; and in specific instances, these will comprise ethoxylated fatty alcohols and/or propoxylated fatty alcohols.

Included ethoxylated fatty alcohols have a linear or branched carbon backbone that has 6-22 carbon atoms and an average of 1-40 ethylene oxide groups. Non-limiting examples of ethoxylated alcohols included in compositions of the present invention are lauryl alcohol ethoxylate, myristyl alcohol ethoxylate, cetyl alcohol ethoxylate, stearyl alcohol ethoxylate, octyldodecanol ethoxylate, and mixtures thereof.

The polyol humectant component of the composition functions as a humectant for the skin and may comprise materials such as glycerin, propylene glycol, butylene glycol, dipropylene glycol, pentylene glycol, hexylene glycol, polyethylene glycol, and the like; and these polyol materials may be used either singly or in combination in the preparations of the present invention.

In specific embodiments of the present invention, the foregoing ingredients are present in particular ratios. In this regard, the fatty alcohols and alkoxylated fatty alcohols are collectively considered to be fatty alcohol excipients, and the polyols are collectively referred to as humectants. In specific compositions of the present invention the ratio of fatty alcohol excipients to humectants to the diisopropyl adipate (DIA) generally comprises, on a weight basis, 30-60 fatty alcohol excipients:30-60 humectants:5-15 DIA. According to aspects of inventive topical lotions, the ratio of fatty alcohols and alkoxylated fatty alcohols:humectants:diisopropyl adipate is, on a weight basis, 39-48:39-50:10-15. In some specific instances, the ratios are 44-46 fatty alcohol excipients:40-43 humectants:11-13 DIA, on a weight basis. An exemplary composition of the present invention comprises a ratio of fatty alcohol excipients 46:humectants 42:DIA 12, on a weight basis. Preparations based upon these ratios will further include the halobetasol material and may also include ancillary ingredients such as preservatives, fragrances, coloring agents, viscosity control agents and the like.

Nonionic surfactants included in topical lotion compositions of the present invention are exemplified by, but not limited to, fatty acid esters and alkoxylated fatty alcohols. One or more additional surfactants is optionally included in topical lotion compositions of the present invention. An included surfactant may be an anionic, cationic or nonionic surfactant. Propoxylated polyoxyethylene ethers, such as poloxamer 407, are non-limiting examples of additional non-ionic surfactants included in topical lotion compositions of the present invention.

One or more preservatives is optionally included in topical lotion compositions of the present invention. Included preservatives are exemplified by, but not limited to parabens, such as methylparaban, ethylparaben, propylparaben, butylparaben and heptylparaben.

Other excipients commonly known as useful in the preparation of topical compositions are further contemplated as within the scope of the present invention. These other materials include, for example, those listed in the current edition of the Ingredients Buyers Guide published by the Personal Care Products Council, 1101 17th Street, NW, Suite 300, Washington D.C. 20036-4702 the entire contents of which are hereby incorporated by reference.

Typically, preparations of the present invention will include a pH adjustment agent as necessary to maintain the product at a pH in the general range of 4.0-6.5 at the time of manufacture, and in particular at a pH of about 5.2-6.2. Such pH adjustment is accomplished by the use of basic materials such as ammonium salts; alkali metal salts, including sodium and potassium salts; alkaline earth metal salts such as calcium and magnesium salts; salts with organic bases such as dicyclohexylamine salts; methyl-D-glucamine; amines, amino acids such as arginine, lysine, and the like, and salts of amino acids. pH adjustment may also be accomplished by the use of nitrogen-containing materials such as quaternized compounds as well as inorganic materials such as sodium, potassium, and ammonium hydroxides.

Viscosity of compositions of the present invention is in the range of 10-70,000 cps. As is well-known in the art, a lotion formulation is an emulsion, pourable at room temperature. A lotion flows at room temperature and conforms to a container when the lotion is inserted into the container at room temperature. A lotion displays Newtonian or pseudoplastic flow behavior, and is generally for external application to the skin. In contrast, creams and ointments are not pourable and do not flow at room temperature and will not conform to a container when placed into the container at room temperature. A cream is an emulsion, semisolid dosage form, usually containing >20% water and volatiles and/or <50% hydrocarbons, waxes, or polyols as the vehicle. A cream dosage form is generally for external application to the skin or mucous membranes. A cream does not flow at low shear stress and generally exhibits plastic flow behavior. Percent water and volatiles in such preparations are measured by a loss on drying test in which the sample is heated at 105° C. until constant weight is achieved. Room temperature is defined as a temperature in the range of 20-25° C.

Figure 2:
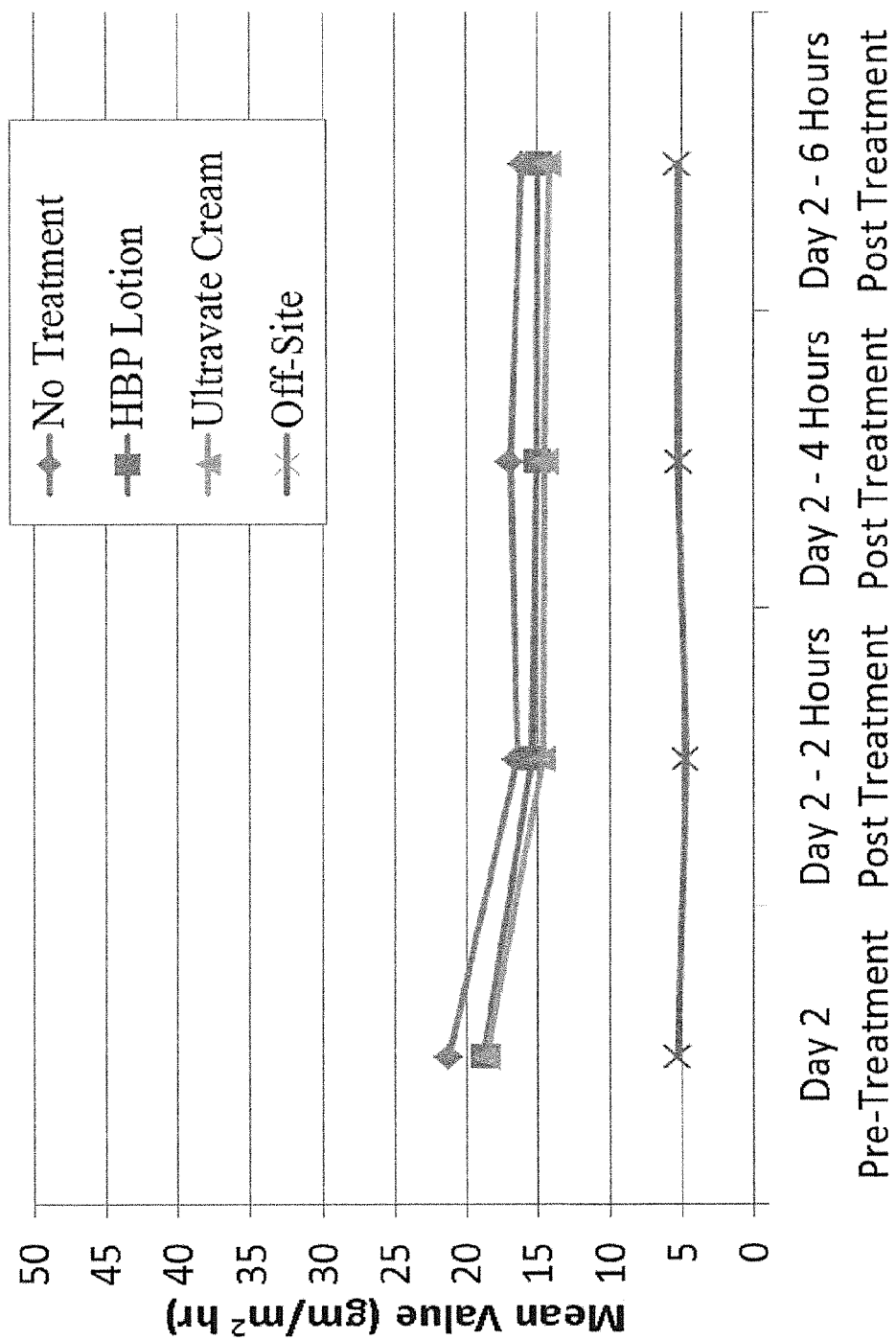
FIG. 2 is a graph showing results of skin water loss analysis comparing a topical lotion composition of the present invention (HBP Lotion) with Ultravate® cream.

As indicated in Wound Care, Lippincott Williams and Wilkins; Ed. Patricia Nale; 2007, page 190, creams are considered more occlusive than lotions. Creams do not have to be applied as often as lotions and are generally considered better for preventing moisture loss due to evaporation. It is surprising and unexpected that lotion compositions of the present invention are statistically indistinguishable from a cream formulation, Ultravate cream, in tests of transepidermal water loss compared to a control, see FIG. 2. The formulation of Ultravate®cream is known in the art to be composed of 0.05% w/w halobetasol propionate, 3% w/w isopropyl isostearate, 2% w/w isopropyl palmitate, 3% w/w steareth-213, 6% w/w cetyl alcohol, 2% w/w glycerin, 0.05% w/w Kathon CG and 0.2% w/w Germall II, see U.S. Pat. No. 5,326,566.

One or more viscosity control agents may be included in order to adjust to the desired viscosity. Viscosity control agents that may be included are exemplified by, but not limited to, one or more cross-linked polyacrylates, such as carbomers. Carbomers also function as emulsion stabilizers.

The compositions of the present invention are found to exhibit very good stability under storage conditions. As is known in the art, halobetasol propionate can degrade under storage conditions, and some of the degradation products or impurities produced thereby include: diflorasone 17-propionate; diflorasone 21-propionate; diflorasone 17-propionate, 21-mesylate; diflorasone 17-propionate, 21-acetate; halobetasol $\Delta_{16}$ analog; halobetasol spiro analog; and B16AN.

Topical lotions of the present invention are storage stable such that the amount of degradation of a halobetasol material therein after storage for six months at 40° C. is <1.5% of the total amount of the halobetasol material contained therein at the time of manufacture, the amount of degradation of the halobetasol material after storage for 26 months at 30° C. is <1% of the total amount of the halobetasol material contained therein at the time of manufacture, and the amount of degradation of the halobetasol material after storage at 25° C. for 30 months is <3% of the halobetasol material contained therein at the time of manufacture.

The amount of degradation products of halobetasol material, such as degradation products of halobetasol propionate, is directly related to the amount of degradation of the halobetasol material. Thus, topical lotions of the present invention are storage stable such that the amount of degradation products of a halobetasol material therein after storage for six months at 40° C. is <1.5% of the total amount of the halobetasol material contained therein at the time of manufacture, the amount of degradation products of the halobetasol material after storage for 26 months at 30° C. is <1% of the total amount of the halobetasol material contained therein at the time of manufacture, and the amount of degradation products of the halobetasol material after storage at 25° C. for 30 months is <3% of the halobetasol material contained therein at the time of manufacture.

The storage stability of topical lotions of the present invention can be demonstrated by assay of the amount of halobetasol material, such as halobetasol propionate, and/or by assay of the amount of one or more degradation products of the halobetasol material, such as the amount of degradation products of halobetasol propionate.

In some specific instances, the lotion of the present invention is an emulsified preparation comprising droplets of an oil phase dispersed in an aqueous phase, and the droplets have a mean particle size in the range of 0.1-50 microns, and in more particular instances a mean particle size in the range of about 1 to 10 microns. In some particular instances, the mean particle size of the droplets ranges from about 1.5 to 7 microns.

Topical lotion compositions of the present invention typically contain droplets having a variety of particle sizes in the range of 0.1-50 microns, such as in the range of 0.15-15 microns and in particular aspects, in the range of 0.175-10 microns.

According to aspects of topical lotions of the present invention, the droplets have a mean particle size in the range of 0.1-50 microns and a distribution of particle sizes ranging from 0.1-50 microns, and in more particular instances a mean particle size in the range of about 1 to 10 microns and a distribution of particle sizes ranging from 0.15-15 microns. In some particular instances, the mean particle size of the droplets ranges from about 1.5 to 7 microns and distribution of particle sizes ranges from 0.175-10 microns.

There are a number of formulations which may be prepared in accord with the present invention. Table 1 hereinbelow lists compositional ranges for one such formulation.

TABLE 1

| Component | % W/W |
|---|---|
| Diisopropyl Adipate | 1-5% |
| Octyldodecanol, NF | 5-15% |
| Ceteth-20 | 0.5-2.0% |
| Poloxamer 407, NF | 0.5-2.0% |
| Cetyl Alcohol, NF | 1-3% |
| Stearyl Alcohol, NF | 0.3-2.0% |
| Propylparaben, NF | 0.05-0.2% |
| Butylparaben, NF | 0.02-0.1% |
| Glycerin, USP | 1-5% |
| Propylene Glycol, USP | 5-15% |
| Carbomer Homopolymer, NF | 0.1-0.2% |
| Sodium Hydroxide, NF | As necessary to adjust pH |
| Halobetasol Propionate, USP | 0.02-0.1% |
| Purified Water, USP | To make 100% |

In this composition, ceteth-20 is a polyethylene glycol-1000 cetyl alcohol ether, and other similar materials may be substituted therefor.

Poloxamer 407 is a particular hydrophilic nonionic surfactant comprising a triblock copolymer consisting of a central hydrophobic block of polypropylene glycol flanked by two hydrophilic blocks of polyethylene glycol. Other such surfactants may be substituted therefor.

The present preparation further includes parabens, specifically propylparaben and butylparaben; and as is known in the art, these materials are antimicrobial agents which function as preservatives.

The composition further includes carbomer 980 which is a cross-linked polyacrylate gelling agent, and other such viscosity control agents may be substituted therefor.

The composition is preferably adjusted to a pH in the range of 5-6.5, and in particular instances 5.2-6.2 and this may be accomplished by the use of an alkali such as sodium hydroxide, potassium hydroxide, or the like.

As discussed above, the topical lotion compositions of the present invention may be fabricated as emulsified materials; and in a general procedure for doing so, one portion of the components is dissolved in water to prepare an aqueous phase. This phase is typically maintained at an elevated temperature in the range of 50-70° C. A second portion of the components is used to prepare a nonaqueous oil phase, and this oil phase is then mixed into the aqueous phase under conditions which will favor formation of an emulsion structure. This mixing is carried out at an elevated temperature, again typically in the range of 50-70° C. Following mixing, the composition is cooled to form a thickened emulsified lotion.

Methods of Treatment

Methods and topical lotion compositions of the present invention are useful for use in the treatment of corticosteroid-responsive dermatoses.

Methods for treating corticosteroid-responsive dermatoses provided herein includes topical administration of a dermal topical lotion composition of the present invention to a patient in need thereof.

Particular corticosteroid-responsive dermatoses treated using methods and topical lotion compositions of the present invention include but are not limited to: dermatitis, including but not limited to atopic dermatitis, seborrhoeic dermatitis, and contact dermatitis; psoriasis; eczemas, including but not limited to atopic, infantile, and discoid eczemas; lichen simplex; lichen planus; reactions to insect and spider bites; miliaria, pityriasis rosea, erythema, and pruritus. Methods and topical lotion compositions of the present invention can be used for prophylaxis as well as amelioration of signs and/or symptoms of corticosteroid-responsive dermatoses. The terms "treating" and "treatment" used to refer to treatment of a corticosteroid-responsive dermatosis in a patient include: preventing, inhibiting or ameliorating the corticosteroid-responsive dermatosis in the patient, such as slowing progression of the corticosteroid-responsive dermatosis and/or reducing or ameliorating a sign or symptom of the corticosteroid-responsive dermatosis.

A therapeutically effective amount of a topical lotion composition of the present invention is an amount which has a beneficial effect on a corticosteroid-responsive dermatosis in a patient being treated. For example, a therapeutically effective amount of a topical lotion composition of the present invention is effective to detectably decrease itching and/or inflammation in a patient being treated for corticosteroid-responsive dermatosis.

Patients are identified as having, or at risk of having, a corticosteroid-responsive dermatosis using well-known medical and diagnostic techniques.

The term "patient" refers to an individual in need of treatment for a corticosteroid-responsive dermatosis. Human patients are particularly referred to herein although the term "patient" is not limited to humans and encompasses mammals and birds, such as, but not limited to, non-human primates, cats, dogs, cows, horses, rodents, pigs, sheep, goats and poultry, and other animals in need of treatment for a corticosteroid-responsive dermatosis seen in veterinary practice.

An inventive composition may be administered acutely or chronically. For example, a topical lotion composition as described herein may be administered topically as a unitary dose or in multiple doses over a relatively limited period of time, such as hours. Administration may include multiple doses administered topically over a period of days—years, such as for chronic treatment of corticosteroid-responsive dermatosis or as multiple short courses of therapy over a period of months or years.

A therapeutically effective amount of a topical lotion composition according to the present invention will vary depending on the particular topical lotion composition used, the severity of the corticosteroid-responsive dermatosis to be treated, the species of the patient, the age and sex of the subject and the general physical characteristics of the patient to be treated. One of skill in the art could determine a therapeutically effective amount in view of these and other considerations typical in medical practice. In general it is contemplated that a therapeutically effective amount, applied topically, would be in the range of about 0.001 mg/kg-150 mg/kg body weight, optionally in the range of about 0.01-10 mg/kg, and further optionally in the range of about 0.1-5 mg/kg. Further, dosage may be adjusted depending on whether treatment is to be acute or continuing.

Treatment of a patient having a corticosteroid-responsive dermatosis by topical administration of a topical lotion composition of the present invention to the affected area is effective to reduce transepidermal water loss in the affected area over a range of greater than 0 and up to about 100%.

Treatment of a patient having a corticosteroid-responsive dermatosis by topical administration of a topical lotion composition of the present invention to the affected area is effective to reduce transepidermal water loss in the affected area by at least 10%, in the range of at least 10% to about 40% and/or by at least 12% to 25%.

Treatment of a patient having a corticosteroid-responsive dermatosis by topical administration of a topical lotion composition of the present invention to the affected area is effective to produce an improvement in skin surface hydration levels of the affected area, as measured by determining skin conductance and/or capacitance. Methods and devices for determining skin conductance and/or capacitance are well-known in the art, for example as described in Clarys P et al., Skin Res Technol. 2012, 18(3):316-23. A commercially available device for measuring skin conductance is the Skicon-200 skin surface hygrometer.

Improvement in skin surface hydration levels of the affected area is observed at 2 hours post treatment and/or at 4 hours post treatment.

Methods of treatment according to the present invention optionally include preparation of the area to be treated by cleansing with a suitable surfactant containing composition.

Combination Treatments

Combinations of therapeutic agents are administered according to aspects of the present invention. According to aspects of methods of the present invention, a topical lotion composition of the present invention is administered topically to a patient having a corticosteroid-responsive dermatosis and at least one additional therapeutic agent is administered to the patient to treat the corticosteroid-responsive dermatosis. In still further aspects, a topical lotion composition of the present invention is administered topically to a patient having a corticosteroid-responsive dermatosis and at least two additional therapeutic agents are administered to the patient to treat the corticosteroid-responsive dermatosis.

The term "additional therapeutic agent" is used herein to denote a chemical compound, a mixture of chemical compounds, a biological macromolecule, such as a lipid, carbohydrate, nucleic acid, a protein or portion thereof, e.g., a peptide, an antibody, a cytokine, or an extract made from biological materials such as bacteria, plants, fungi, or animal, particularly mammalian, cells or tissues which is a biologically, physiologically, or pharmacologically active substance, or substances, that acts locally or systemically in a patient to provide a beneficial effect in treatment of a corticosteroid-responsive dermatosis.

Additional therapeutic agents included in aspects of methods and compositions of the present invention include, but are not limited to, antibiotics, antivirals, antifungals, analgesics, antipyretics, antihistamines, antiinflammatory agents, anxiolytics, cytokines, non-steroidal antiinflammatory agents, steroids and vasoactive agents.

Combination therapies utilizing a topical lotion composition of the present invention and one or more additional therapeutic agents may show synergistic effects, e.g., a greater therapeutic effect than would be observed using either the topical lotion composition of the present invention or one or more additional therapeutic agents alone as a monotherapy.

According to aspects, combination therapies include: (1) pharmaceutical compositions that include a topical lotion composition of the present invention in combination with one or more additional therapeutic agents; and (2) co-administration of a topical lotion composition of the present invention with one or more additional therapeutic agents wherein the topical lotion composition of the present invention and the one or more additional therapeutic agents have not been formulated in the same composition. When using separate formulations, the topical lotion composition of the present invention may be administered at the same time, intermittent times, staggered times, prior to, subsequent to, or combinations thereof, with reference to the administration of the one or more additional therapeutic agents.

Combination treatments can allow for reduced effective dosage and increased therapeutic index of the topical lotion composition of the present invention and the one or more additional therapeutic agents used in methods of the present invention.

Additional therapeutic agents included in methods and/or compositions of the present invention are described, for example, in Goodman et al., Goodman and Gilman's The Pharmacological Basis of Therapeutics, 12th Ed., McGraw-Hill Professional, 2010.

Commercial Packages

Commercial packages provided herein include a topical lotion composition of the present invention in a container suitable for storage and delivery of the topical lotion composition.

A container suitable for storage and delivery of the topical lotion composition can be any of various sizes or shapes useful for containing and/or delivering the topical lotion composition exemplified by, but not limited to, a pump, canister, jar, bottle, tube, sachet, or vial.

Optionally, the container is comprised of a ferrous alloy, aluminum, glass, plastic, polymer, or combinations thereof. The container further optionally includes one or more protective coatings.

A container for a topical lotion composition of the present invention optionally includes at least two separate compartments wherein the topical lotion composition is disposed in one of the compartments. A second therapeutic agent may be contained in a second compartment, separate from the topical lotion composition of the present invention, and may be dispensed therefrom for direct use, or may be mixed with the topical lotion composition of the present invention prior to use. For example, a barrier between separate compartments may be pierced or removed to allow for mixing of the topical lotion composition and the material in a second compartment. In another application, the topical lotion may be dispensed in combination with a second active pharmaceutical ingredient for a number of dispensations after which only the topical lotion or the second active pharmaceutical ingredient is dispensed.

A topical lotion composition of the present invention may be deposited on a bandage or dressing for application to a region affected by a corticosteroid-responsive dermatosis.

Instructions for use of a topical lotion composition of the present invention are optionally included in a commercial package, wherein the instructions are directed to a physician and/or to the patient. Included instructions to the patient optionally include instructions to prepare the area to be treated by cleansing with a suitable surfactant containing composition.

Embodiments of inventive compositions and methods are illustrated in the following examples. These examples are provided for illustrative purposes and are not considered limitations on the scope of inventive compositions and methods.

EXAMPLES

Example 1

In one specific procedure, a lotion is prepared in accord with the present invention utilizing the formulation of Table 2. Listed in Table 2 is a specific composition based upon the ranges set forth hereinabove.

TABLE 2

| Component | % W/W | Quantity |
|---|---|---|
| Diisopropyl Adipate | 3.50% | 105.0 g |
| Octyldodecanol, NF | 10.00% | 300.0 g |
| Ceteth-20 | 1.00% | 30.0 g |
| Poloxamer 407, NF | 1.00% | 30.0 g |
| Cetyl Alcohol NF | 2.00% | 60.0 g |
| Stearyl Alcohol, NF | 0.66% | 19.8 g |
| Propylparaben, NF | 0.10% | 3.0 g |
| Butylparaben, NF | 0.05% | 1.5 g |
| Glycerin, USP | 2.50% | 75.0 g |
| Propylene Glycol, USP | 10.00% | 300.0 g |
| Carbomer Homopolymer, NF | 0.15% | 4.5 g |
| Sodium Hydroxide, NF | 0.012% | 0.36 g |
| Halobetasol Propionate, USP | 0.05% | 1.5 g |
| Purified Water, USP | 68.978% | 2069.34 g |
| Total % | 100% | |
| Theoretical Total Weight | | 3000.0 g |

In this procedure, an aqueous phase is prepared by mixing water with the glycerin, and propylene glycol. These materials are then mixed at a temperature of approximately 65° C. A second mixture comprising a DIA, octyldodecanol, ceteth-20, poloxamer 407, cetyl alcohol, stearyl alcohol, parabens, and halobetasol. This mixture is stirred at approximately 65° C. for a period of time sufficient to dissolve the halobetasol material. The resulting aqueous and oil phases are disposed in a high shear emulsifier and mixed at a speed of approximately 6000 rpm to produce a homogenized mixture. Carbomer is added, followed by another high shear mixing and then neutralization with base. The resultant mixture is cooled with mixing to a temperature of approximately 30° C. under vacuum, after which the preparation is complete. Clearly, modifications and variations of this procedure will be readily apparent to those of skill in the art.

Example 2

A series of studies was carried out to evaluate the properties and advantages of the compositions of the present invention. These studies were carried out utilizing an emulsified lotion preparation having a formulation in accord with Table 2 as prepared by the procedure set forth above. In a first study, the efficacy of the composition with regard to skin hydration was determined utilizing a Skicon-200 apparatus which determined the net change in skin conductance as a function of time, following application of a material. Compositions of the present invention were compared with the industry standard Ultravate® Cream and with a shaved skin control sample. The resultant data are summarized in FIG. 1. As will be seen from FIG. 1, skin conduction increased very rapidly at the 2 hour point for the composition of the present invention as compared to the Ultravate® Cream and the control. At the 4 hour point, it will be seen that skin conductance of the Ultravate® Cream has risen while that of the composition of the present invention has fallen, although it is still higher than that of the Ultravate® Cream. At the 6 hour point, the composition of the present invention and the Ultravate® Cream both have similar skin conductance measurements. The data of experiment and FIG. 1 make clear that the composition of the present invention very rapidly promotes skin hydration whereas the action of the Ultravate® Cream is both slower and of less magnitude in this regard. The data confirm that the composition of the present invention produced a rapid onset and sustained action of the therapeutic effect. This unexpected finding was validated at both the 2 and 4-hour time points where the conductance of the halobetasol lotion was statistically significantly ($p<0.001$) greater than that of the Ultravate® Cream.

Statistical Summary for Net Change in Skicon Conductance at 2, 4 and 6 Hrs Post Treatment is shown in Table 3.

TABLE 3

Net Change in Skicon Conductance
(N = 15)
Statistical Differences
Multiple Comparisons

| Comparison | 2 Hours[a] | 4 Hours[a] | 6 Hours[b] |
|---|---|---|---|
| HBP Lotion > Ultravate Cream | p < 0.001 | p < 0.001 | p > 0.05 |
| HBP Lotion > NoRx shaved | p < 0.001 | p < 0.001 | p < 0.001 |
| Ultravate Cream > NoRx shaved | p > 0.05 | p > 0.05 | p < 0.05 |

[a]Tukey-Kramer Multiple Comparisons Test
[b]Dunn's Multiple Comparisons Test

Example 3

A study was carried out measuring transepidermal water loss (TEWL) of skin treated with the lotion of the present invention and skin treated with Ultravate® Cream, as compared to a dry shaved control. Computerized evaporimetry was carried out utilizing a state of the art Derm RG-1 Evaporometer; a research grade and open-chamber device based on the time proven vapor pressure gradient estimation method pioneered by Gert Nilsson. Data from this evaluation are summarized in FIG. 2 and it will be seen that over the 6 hour course of the study, the lotion of the present invention was at least as effective as the Ultravate® Cream of the prior art in preventing water loss. This finding is unexpected in view of conventional wisdom in the prior art which holds that with regard to minimizing TEWL the efficacy of ointments is greater than that of creams/gels, which is greater than that of lotions, which is greater than that of simple solutions. Therefore, the study further evidences the unexpected and beneficial results attendant upon the present invention.

Neither test product seems to be acting as an occlusive since TEWL remains the same as the non-treated shaved control. There were no statistically significant treatment differences at any time point.

Example 4

A further experimental study evaluated the clinical efficacy of the lotion of the present invention having the formulation described above, in the treatment of subjects with plaque psoriasis. The study involved a double-blind, randomized, multicenter, vehicle-controlled parallel group study involving a 2 week course of treatment. The efficacy and safety of a topical lotion composition of the present invention including halobetasol propionate (HBP) 0.05%, applied twice daily for 14 consecutive days in subjects with moderate to severe plaque psoriasis was determined and compared with Vehicle Lotion applied twice daily for 14 consecutive days in subjects with moderate to severe plaque psoriasis. The study involved 72 subjects, with approximately 36 per treatment group, and was carried out at three separate sites with approximately 24 subjects at each site. Subjects were selected so that their plaque psoriasis involved a minimum of 2% and no more than approximately 10% of their BSA (excluding the face, scalp, groin, axillae, and other intertriginous areas).

Definitions: In this study "treatment success" is indicated by a score of 0 or 1 for overall disease severity (ODS) and the clinical signs and symptoms of psoriasis. Further, the term "improved" refers to at least a two (2) grade decrease in severity score relative to Baseline for overall disease severity (ODS) and the clinical signs and symptoms of psoriasis. Note: Dichotomization of scores for clinical signs and symptoms of psoriasis will exclude subjects with Baseline scores of 0 or 1 unless the corresponding sign score at Day 8 or Day 15 is >1.

Efficacy Endpoints included a primary efficacy endpoint and secondary efficacy endpoints. The primary efficacy endpoint is the proportion of subjects with Overall Disease Severity (ODS) "treatment success" at End of Treatment (EOT) where EOT is the last visit (Day 8 if early termination or Day 15) with Last Observation Carried Forward (LOCF) imputation for early terminations. Secondary efficacy endpoints are: 1) the proportion of subjects with ODS "treatment success" at Day 8 and Day 15 (no LOCF imputation); and 2) the proportion of subjects rated "improved" with respect to ODS at Days 8 and 15, respectively.

Additional details of the study design and results of this study are shown in TABLES 4-8.

TABLE 4

Screening/Enrollment-Study Summary

| Investigator | Enrollment information | | Subject's Final Disposition | | |
|---|---|---|---|---|---|
| | Total Screened | Total Enrolled | Screen Failures | Total Completed | Total Early Terms |
| Site 01 | 24 | 24 | 0 | 23 | 1 |
| Site 02 | 24 | 24 | 0 | 24 | 0 |
| Site 03 | 25 | 24 | 1 | 24 | 0 |
| Totals | 73 | 72 | 1 | 71 | 1 |

TABLE 5

Overall Disease Severity (ITT Population) Observed

| | HBP N (%) | VEH N (%) | ALL N (%) |
|---|---|---|---|
| BASELINE | | | |
| Clear | 0 (0.0%) | 0 (0.0%) | 0 (0.0%) |
| Almost Clear | 0 (0.0%) | 0 (0.0%) | 0 (0.0%) |
| Mild | 0 (0.0%) | 0 (0.0%) | 0 (0.0%) |
| Moderate | 30 (83.3%) | 30 (85.7%) | 60 (84.5%) |
| Severe/Very Severe | 6 (16.7%) | 5 (14.3%) | 11 (15.5%) |
| All | 36 (100.0%) | 35 (100.0%) | 71 (100.0%) |
| DAY 8 | | | |
| Clear | 0 (0.0%) | 0 (0.0%) | 0 (0.0%) |
| Almost Clear | 2 (5.6%) | 0 (0.0%) | 2 (2.8%) |
| Mild | 16 (44.4%) | 6 (17.1%) | 22 (31.0%) |
| Moderate | 18 (50.0%) | 26 (74.3%) | 44 (62.0%) |
| Severe/Very Severe | 0 (0.0%) | 3 (8.6%) | 3 (4.2%) |
| All | 36 (100.0%) | 35 (100.0%) | 71 (100.0%) |
| DAY 15 | | | |
| Clear | 2 (5.6%) | 0 (0.0%) | 2 (2.8%) |
| Almost Clear | 9 (25.0%) | 0 (0.0%) | 9 (12.7%) |
| Mild | 16 (44.4%) | 6 (17.1%) | 22 (31.0%) |
| Moderate | 9 (25.0%) | 25 (71.4%) | 34 (47.9%) |
| Severe/Very Severe | 0 (0.0%) | 4 (11.4%) | 4 (5.6%) |
| All | 36 (100.0%) | 35 (100.0%) | 71 (100.0%) |

ITT = intent-to-treat;
HBP = halobetasol propionate;
VEH = vehicle

TABLE 6

Overall Disease Severity (ITT Population) Change From Baseline

| | HBP N (%) | VEH N (%) | ALL N (%) |
|---|---|---|---|
| DAY 8 | | | |
| −2 | 5 (13.9%) | 0 (0.0%) | 5 (7.0%) |
| −1 | 16 (44.4%) | 8 (22.9%) | 24 (33.8%) |
| 0 | 15 (41.7%) | 27 (77.1%) | 42 (59.2%) |
| ALL | 36 (100.0%) | 35 (100.0%) | 71 (100.0%) |
| DAY 15 | | | |
| −3 | 3 (8.3%) | 0 (0.0%) | 3 (4.2%) |
| −2 | 13 (36.1%) | 0 (0.0%) | 13 (18.3%) |
| −1 | 11 (30.6%) | 8 (22.9%) | 19 (26.8%) |
| 0 | 9 (25.0%) | 26 (74.3%) | 35 (49.3%) |
| 1 | 0 (0.0%) | 1 (2.9%) | 1 (1.4%) |
| ALL | 36 (100.0%) | 35 (100.0%) | 71 (100.0%) |

ITT = intent-to-treat;
HBP = halobetasol propionate;
VEH = vehicle

TABLE 7

Overall Disease Severity (ITT Population) Success

|  | HBP N (%) | VEH N (%) | ALL N (%) |
|---|---|---|---|
| DAY 8 | | | |
| YES | 2 (5.6%) | 0 (0.0%) | 2 (2.8%) |
| NO | 34 (94.4%) | 35 (100.0%) | 69 (97.2%) |
| ALL | 36 (100.0%) | 35 (100.0%) | 71 (100.0%) |
| DAY 15 | | | |
| YES | 11 (30.6%) | 0 (0.0%) | 11 (15.5%) |
| NO | 25 (69.4%) | 35 (100.0%) | 60 (84.5%) |
| ALL | 36 (100.0%) | 35 (100.0%) | 71 (100.0%) |

ITT = intent-to-treat;
HBP = halobetasol propionate;
VEH = vehicle
Day 15: Fisher's Exact test p < 0.001

TABLE 8

Overall Disease Severity (ITT Population) Improved

|  | HBP N (%) | VEH N (%) | ALL N (%) |
|---|---|---|---|
| DAY 8 | | | |
| YES | 5 (13.9%) | 0 (0.0%) | 5 (7.0%) |
| NO | 31 (86.1%) | 35 (100.0%) | 66 (93.0%) |
| ALL | 36 (100.0%) | 35 (100.0%) | 71 (100.0%) |
| DAY 15 | | | |
| YES | 16 (44.4%) | 0 (0.0%) | 16 (22.5%) |
| NO | 20 (55.6%) | 35 (100.0%) | 55 (77.5%) |
| ALL | 36 (100.0%) | 35 (100.0%) | 71 (100.0%) |

ITT = intent-to-treat;
HBP = halobetasol propionate;
VEH = vehicle

The topical lotion composition of the present invention exhibited very good results in the treatment of plaque psoriasis, showing treatment being a complete success with regard to 30.6% of the patients studied, and producing significant improvement with regard to 44.4% of the patients in the study. These results are very strong and significant particularly as compared to those achieved through the use of Ultravate® Cream and other comparable prior art compositions.

Example 5

TABLE 9 compares the results for the halobetasol propionate lotion as achieved in the present study, to those previously obtained utilizing FDA approved compositions of the prior art.

TABLE 9

FDA Approved Class 1 Topical Corticosteroid Products (1-9) and Halobetasol Propionate Lotion, the present invention (10 and 11) "Treatment Success" at 2 Weeks

|  | Study Drug | Results | Control Drug | Results | Year Approved |
|---|---|---|---|---|---|
| 1 | Ultravate Cream (Study 1) | 3/38 (7.9%) | Vehicle | 0/39 (0.0%) | 1991 |
| 2 | Ultravate Cream (Study 2) | 7/40 (17.5%) | Vehicle | 0/40 (0.0%) | 1991 |
| 3 | Temovate E ITT | 12/51 (22%) | Vehicle | 1/46 (2%) Note: includes Cleared and Excellent | 1994 |
| 4 | Clobetasol Lotion ITT 4 wk. study | 30/82 (36.6%) | Temovate E | 33/81 (40.7%) | 2003 |
| 5 | Clobetasol Lotion PP 4 wk. study | 27/76 (35.5%) | Temovate E PP | 32/75 (42.7%) | 2003 |
| 6 | Vanos QD ITT | 19/107 (18%) | Vanos BID ITT | 33/107 (31%) | 2005 |
| 7 | Vanos QD PP | 18/90 (20%) | Vanos BID PP | 31/97 (32%) | 2005 |
| 8 | Olux E ITT | 41/253 (16%) | Temovate Ointment | 38/121 (31%) | 2007 |
| 9 | Olux E PP | 39/234 (17%) | Temovate Ointment | 34/111 (31%) | 2007 |
| 10 | Halobetasol Lotion (P2) ITT | 11/36 (30.6%) | Vehicle | 0/35 (0.0%) | (Success) 2012 |
| 11 | Halobetasol Lotion (P2) ITT | 16/36 (44.4%) | Vehicle | 0/35 (0.0%) | (Improved) 2012 |

In the current Halobetasol Lotion study "Treatment Success" is defined at the End of Treatment as a score of 0 or 1 for overall disease severity (ODS) and clinical signs and symptoms of psoriasis. "Improved" means subjects had at least a two (2) grade decrease in severity score relative to Baseline for overall disease severity (ODS) and the clinical signs and symptoms of psoriasis.

It should be noted that over the years the FDA has changed the parameters defining clinical "success" and has each time raised the bar. The results obtained with the present halobetasol propionate lotion were unexpectedly strong. The Ultravate® Cream results as shown in the first two rows of the TABLE 9 were filed with the FDA as a basis of an NDA approval, and it will be seen that the results achieved with the halobetasol propionate lotion of the present invention are superior to those achieved through the use of the Ultravate® Cream and are as good or better than any of the other Class 1 topical corticosteroids. It will be noted that the clobetasol propionate lotion results are similar to those achieved utilizing the present halobetasol propionate lotion; however, clobetasol propionate is generally believed to be a more potent steroid molecule than halobetasol propionate, and furthermore the clobetasol propionate studies ran for 4 weeks as compared to 2 weeks for the study involving the halobetasol propionate composition of the present invention. These results are unexpected given the relative potencies of halobetasol propionate and clobetasol propionate, and given the longer duration of the clobetasol propionate treatment. These results show unexpected therapeutic effects achieved through the composition of the present invention.

Example 6

Six formulations were prepared including various amounts and ratios of components. Three lotions, designated 30124-1, 30125-1 and 30125-2, had compositions with ratios of 30-60:30-60:5-15 for fatty alcohol excipients (fatty alcohols and alkoxylated fatty alcohols):humectants:DIA; and three formulations, designated 30128-1, 30129-1 and 30130-1, had compositions outside of these ratio ranges. The formulations are summarized in TABLE 10 below where the composition changes from the clinical formulation of Example 1 are underlined.

stabilization of the emulsion included in compositions of the present invention. Formulation 30128-1 was prepared with higher levels of these excipients and would be expected to be stable. However, the initial appearance of this formulation was a thick and nonpourable emulsion. A key attribute of a topical lotion composition of the present invention is that it is pourable and easy to spread. Therefore, even though 30128-1 was expected to be more stable than formulations that had

TABLE 10

| | Formula name | | | | | |
|---|---|---|---|---|---|---|
| | 30124-1 | 30125-1 | 30125-2 | 30128-1 | 30129-1 | 30130-1 |
| Component | Component Amount % w/w | | | | | |
| Halobetasol propionate | 0.05 | 0.05 | 0.05 | 0.05 | 0.05 | 0.05 |
| DIA | 4.5 | 3.5 | 3.5 | 3.5 | 0.75 | 3.5 |
| Octyldodecanol | 10 | 10 | 10 | 10 | 10 | 10 |
| Ceteth-20 | 1 | 1 | 1 | 3 | 1 | 1 |
| Poloxamer 407 | 1 | 1 | 1 | 1 | 1 | 1 |
| Cetyl alcohol | 2 | 2 | 2.5 | 5 | 2 | 2 |
| Stearyl alcohol | 0.66 | 0.66 | 1 | 3 | 0.66 | 0.66 |
| Propylparaben | 0.1 | 0.1 | 0.1 | 0.1 | 0.1 | 0.1 |
| Butylparaben | 0.05 | 0.05 | 0.05 | 0.05 | 0.05 | 0.05 |
| Glycerin | 2.5 | 5 | 2.5 | 1 | 2.5 | 2.5 |
| Propylene glycol | 9 | 12.5 | 10 | 7.5 | 10 | 0 |
| Carbomer 980 | 0.15 | 0.15 | 0.15 | 0.15 | 0.15 | 0.15 |
| 1.0N NaOH | q.s. pH 5.5 | q.s. pH 5.5 | q.s. pH 5.5 | q.s. pH 5.5 | q.s. pH 5.5 | q.s. pH 5.5 |
| Water | q.s. 100% | q.s. 100% | q.s. 100% | q.s. 100% | q.s. 100% | q.s. 100% |
| | Ratio | Ratio | Ratio | Ratio | Ratio | Ratio |
| fatty alcohols and ethoxylated fatty alcohols | 46 | 39 | 48 | 64 | 51 | 69 |
| Humectants | 39 | 50 | 41 | 26 | 46 | 13 |
| DIA | 15 | 10 | 11 | 11 | 3 | 18 |
| Appearance | Pass | Pass | Pass | Fail[1] | Fail[2] | Pass |
| Stability @ 40° C. | Stable for at least 3 months | Stable for at least 3 months | Stable for at least 3 months | N/A | N/A | Fail[3] |

[1]Thick non-pourable cream;
[2]Drug crystals precipitated;
[3]Long term stability failure.

All three formulations 30124-1, 30125-1 and 30125-2, which had compositions with ratios of 30-60:30-60:5-15 for fatty alcohol excipients:humectants:DIA; had acceptable appearance, i.e. a homogeneous pourable lotion. Two of the formulations, 30128-1 and 30129-1, which had compositions outside of the ratios of 30-60:30-60:5-15 for fatty alcohol excipients:humectants:DIA had unacceptable appearance, and the third, 30130-1, had acceptable appearance but failed on stability.

Diisopropyl adipate (DIA) is a solvent for halobetasol propionate (HP). Higher and lower levels of this ingredient were evaluated in this series of experiments. The formulation with higher DIA, 4.5% w/w, (30124-1) produced an acceptable composition. The formulation with a low DIA level 0.75% w/w (30129-1) was successfully prepared in that all of the HP was solubilized. However, surprisingly, this formulation showed drug crystals within 12 hours of preparation, producing unacceptable appearance. This was surprising since there was a significant amount of surfactant and octyldodecanol in the formulation 30129-1 which can also solubilize HP.

The fatty alcohols and alkoxylated fatty alcohols, particularly ethoxylated fatty alcohols, have significant effects on ratios of 30-60:30-60:5-15 for fatty alcohol excipients:humectants:DIA components, 30128-1 had unacceptable physical properties.

Formulation 30130-1 did not include propylene glycol and had a composition outside of the ratio of 30-60:30-60:5-15 for fatty acid excipients:humectants:DIA. Propylene glycol is not known as an emulsion stabilizer. Surprisingly, this composition was found to be unstable on long term storage. The emulsion of formulation 30130-1 showed a phase separation or syneresis.

Thus, compositions of the present invention having ratios of 30-60:30-60:5-15 for fatty alcohol excipients:humectants:DIA components produce topical lotion compositions which are effective in treatment of corticosteroid-responsive dermatoses, have acceptable appearance, are homogeneous pourable lotions and are stable on storage.

Items

1. A storage stable, topical lotion composition for treating a skin disorder or condition, said composition comprising:
a halobetasol material comprising halobetasol or its pharmaceutically acceptable salts, esters, and solvates; and
a pharmaceutically acceptable carrier which includes: (a) one or more fatty alcohols and/or one or more alkoxylated fatty alcohols, (b) one or more polyol humectants, and (c) diisopropyl adipate.

2. The topical lotion of item 1, wherein the fatty alcohol is selected from the group consisting of lauryl alcohol, myristyl alcohol, cetyl alcohol, stearyl alcohol, octyldodecanol, and mixtures of any two or more thereof.

3. The topical lotion of item 1 or item 2, wherein the alkoxylated fatty alcohol is an ethoxylated alcohol selected from the group consisting of lauryl alcohol ethoxylate, myristyl alcohol ethoxylate, cetyl alcohol ethoxylate, stearyl alcohol ethoxylate, octyldodecanol ethoxylate, and mixtures of any two or more thereof.

4. The topical lotion of any of items 1-3, wherein the polyol humectant is selected from the group consisting of glycerin, propylene glycol, butylene glycol, dipropylene glycol, pentylene glycol, hexylene glycol, polyethylene glycol and mixtures of any two or more thereof.

5. The topical lotion of any of items 1-4, wherein the amount of said halobetasol material after storage for six months at 40° C. is >98.5% of the total amount of halobetasol material present at the time of manufacture of the topical lotion, wherein the amount of degradation of said halobetasol material after storage for 26 months at 30° C. is <1% of the total amount of halobetasol material present at the time of manufacture of the topical lotion and wherein the amount of degradation of said halobetasol material after storage at 25° C. for 30 months is <3% of the total amount of halobetasol material present at the time of manufacture of the topical lotion.

The topical lotion of any of items 1-5, wherein the amount of degradation of said halobetasol material after storage for six months at 40° C. is <1.5% of the total amount of said halobetasol material, wherein the amount of degradation of said halobetasol material after storage for 26 months at 30° C. is <1% of said halobetasol material and wherein the amount of degradation of said halobetasol material after storage at 25° C. for 30 months is <3% of said halobetasol material.

7. The topical lotion of any of items 1-6, wherein said halobetasol material is halobetasol propionate.

8. The topical lotion of any of items 1-7, further including one or more members selected from the group consisting of: one or more additional therapeutic agents, coloring agents, preservatives, pH control agents, viscosity control agents, and fragrances.

9. The topical lotion of any of items 1-8, wherein the ratio of said fatty alcohols and alkoxylated fatty alcohols to said humectants, to said diisopropyl adipate is, on a weight basis, in the range of 30-60:30-60:5-15.

10. The topical lotion of any of items 1-9, wherein the ratio of said fatty alcohols and alkoxylated fatty alcohols to said humectants, to said diisopropyl adipate is, on a weight basis, in the range of 39-48:39-50:10-15.

11. The topical lotion of any of items 1-10, wherein the weight ratio of said fatty alcohols and ethoxylated fatty alcohols to said polyol humectants to said diisopropyl adipate is in the range of 44-46:40-43:11-13.

12. The topical lotion of any of items 1-11, wherein the weight ratio of said fatty alcohols and ethoxylated fatty alcohols to said polyol humectants to said diisopropyl adipate is 46:42:12.

13. The topical lotion of any of items 1-12, wherein said topical lotion composition is an oil-in-water emulsion of droplets having a mean particle size in the range of 0.1-50 microns and a distribution of particle sizes in the range of 0.1-50 microns.

14. The topical lotion of any of items 1-13, wherein said topical lotion composition is an oil-in-water emulsion of droplets having a mean particle size in the range of 1-10 microns and a distribution of particle sizes in the range of 0.15-15 microns.

15. The topical lotion of any of items 1-14, wherein said topical lotion composition is an oil-in-water emulsion of droplets having a mean particle size in the range of 1.5-7 microns and a distribution of particle sizes in the range of 0.175-10 microns.

16. A storage stable, topical lotion composition comprising, on a weight basis: 0.02-0.10% of a halobetasol material; 1-5% of diisopropyl adipate; 5-15% octyl dodecanol; 0.50-2% of polyethylene glycol 1000 cetyl ether; 0.50-2% of a surfactant; 1-3% cetyl alcohol; 1-2% stearyl alcohol; 0.05-0.2% of a preservative; 5-15% propylene glycol; 1-5% glycerin; a pH adjustment agent an amount sufficient to adjust the pH of the composition to a range of approximately 5-6.5; and water q.s.

17. The storage stable, topical lotion composition of item 16, further comprising a viscosity control agent in an amount of 0.1-0.5% w/w.

18. A storage stable, topical lotion composition comprising, on a weight basis: 0.05% of a halobetasol material; 3.5% of diisopropyl adipate; 10% octyl dodecanol; 1% of polyethylene glycol 1000 cetyl ether; 1% of a surfactant; 2% cetyl alcohol; 0.66% stearyl alcohol; 0.15% of a preservative such as a paraben preservative, for example propyl paraben and/or butyl paraben; 10% propylene glycol; 2.5% glycerin; a pH adjustment agent in an amount sufficient to adjust the pH of the composition to a range of approximately 5-6.5; and water q.s.

19. The storage stable, topical lotion composition of item 18, further comprising a viscosity control agent in an amount of 0.25% w/w.

20. The topical lotion of any of items 1-19, wherein said halobetasol material is halobetasol propionate.

21. A method for treating corticosteroid-responsive dermatoses comprising: topically administering to a patient in need thereof, the topical lotion composition of any of items 1-20.

22. The method of item 21, wherein said topical lotion composition is packaged in a container suitable for storage and delivery of said composition.

23. The method of item 22, wherein said container is comprised of a ferrous alloy, aluminum, glass, plastic, or combinations thereof.

24. The method of any of items 22-23, wherein said container further includes one or more protective coatings.

25. The method of any of items 22-24, wherein said container includes at least two separate compartments wherein said topical lotion composition of claim 1 is disposed in one of said compartments.

26. The method of any of items 21-25, wherein the patient is further instructed to prepare the area to be treated by cleansing with a suitable surfactant-containing composition.

27. The method of any of items 21-26, wherein said method is as effective to reduce transepidermal water loss as a cream formulation compared to a shaved skin control.

28. The method of any of items 21-27, wherein said method is as effective to reduce transepidermal water loss as Ultravate® cream compared to a shaved skin control.

29. The method of any of items 21-28, wherein said method is effective to produce an improvement in skin surface hydration levels as measured with a skin conductance or capacitance measuring apparatus.

30. The method of any of items 21-29, wherein said method is effective to produce an improvement in skin surface hydration levels as measured with a skin conductance or capacitance measuring apparatus, wherein said improvement is observed at 2 hours post treatment.

31. The method of any of items 21-30, wherein said method is effective to produce an improvement in skin surface hydration levels as measured with a skin conductance or capacitance measuring apparatus, wherein said improvement is observed at 4 hours post treatment.

32. A method for the preparation of the topical lotion composition of any of items 1-19, said method comprising the steps of: preparing an aqueous phase that includes a first portion of the components of said topical lotion composition; maintaining said aqueous phase at a temperature in the range of 45-70° C.; preparing an oil phase that includes a second portion of the components of said topical lotion composition; adding said oil phase to said aqueous phase while stirring at a temperature of about 45-70° C. so as to obtain an emulsion; cooling said emulsion to a temperature of about 25-35° C.; and adjusting the pH of said emulsion to a pH in the range of 5.0-6.5.

The present invention provides therapeutic compositions which have unexpected therapeutic efficacy in the treatment of dermatoses. The lotion compositions of the present invention readily penetrate the skin to provide a rapid therapeutic effect and operate to promote hydration and limit water loss of the skin. While the foregoing describes some particular compositions based on therapeutically active halobetasol materials, it will be readily apparent to those of skill in the art that the principles of the present invention may be readily extended to other corticosteroids as well as other therapeutically active ingredients. All of such modifications and variations thereof may be implemented by those of skill in the art, without undue experimentation. The foregoing drawings, discussion, and description are illustrative of specific embodiments of the invention but are not meant to be limitations upon the practice thereof. It is the following claims, including all equivalents, which define the scope of the invention.

The invention claimed is:

1. A storage stable, topical lotion composition for treating a skin disorder or condition, said composition comprising: a halobetasol material comprising halobetasol or its pharmaceutically acceptable salts, esters, and solvates; and a pharmaceutically acceptable carrier which includes: (a) one or more fatty alcohols and/or one or more alkoxylated fatty alcohols, (b) one or more polyol humectants, and (c) diisopropyl adipate, wherein the amount of said halobetasol material after storage for six months at 40° C. is >98.5% of the total amount of halobetasol material present at the time of manufacture of the topical lotion, wherein the amount of degradation of said halobetasol material after storage for 26 months at 30° C. is <1% of the total amount of halobetasol material present at the time of manufacture of the topical lotion and wherein the amount of degradation of said halobetasol material after storage at 25° C. for 30 months is <3% of the total amount of halobetasol material present at the time of manufacture of the topical lotion, and
wherein the ratio of said fatty alcohols and alkoxylated fatty alcohols to said humectants, to said diisopropyl adipate is, on a weight basis, in the range of 30-60:30-60:5-15.

2. The topical lotion of claim 1, wherein the fatty alcohol is selected from the group consisting of lauryl alcohol, myristyl alcohol, cetyl alcohol, stearyl alcohol, octyldodecanol, and mixtures of any two or more thereof.

3. The topical lotion of claim 1, wherein the alkoxylated fatty alcohol is an ethoxylated alcohol selected from the group consisting of lauryl alcohol ethoxylate, myristyl alcohol ethoxylate, cetyl alcohol ethoxylate, stearyl alcohol ethoxylate, octyldodecanol ethoxylate, and mixtures of any two or more thereof.

4. The topical lotion of claim 1, wherein the polyol humectant is selected from the group consisting of glycerin, propylene glycol, butylene glycol, dipropylene glycol, pentylene glycol, hexylene glycol, polyethylene glycol and mixtures of any two or more thereof.

5. The topical lotion of claim 1, wherein the amount of degradation of said halobetasol material after storage for six months at 40° C. is <1.5% of the total amount of said halobetasol material, wherein the amount of degradation of said halobetasol material after storage for 26 months at 30° C. is <1% of said halobetasol material and wherein the amount of degradation of said halobetasol material after storage at 25° C. for 30 months is <3% of said halobetasol material.

6. The topical lotion of claim 1, wherein said halobetasol material is halobetasol propionate.

7. The topical lotion of claim 1, further including one or more members selected from the group consisting of: one or more additional therapeutic agents, coloring agents, preservatives, pH control agents, viscosity control agents, and fragrances.

8. The topical lotion of claim 1, wherein the ratio of said fatty alcohols and alkoxylated fatty alcohols to said humectants, to said diisopropyl adipate is, on a weight basis, in the range of 39-48:39-50:10-15.

9. The topical lotion of claim 1, wherein the weight ratio of said fatty alcohols and ethoxylated fatty alcohols to said polyol humectants to said diisopropyl adipate is in the range of 44-46:40-43:11-13.

10. The topical lotion of claim 1, wherein the weight ratio of said fatty alcohols and ethoxylated fatty alcohols to said polyol humectants to said diisopropyl adipate is 46:42:12.

11. The topical lotion of claim 1, wherein said topical lotion composition is an oil-in-water emulsion of droplets having a mean particle size in the range of 0.1-50 microns and a distribution of particle sizes in the range of 0.1-50 microns.

12. The topical lotion of claim 1, wherein said topical lotion composition is an oil-in-water emulsion of droplets having a mean particle size in the range of 1-10 microns and a distribution of particle sizes in the range of 0.15-15 microns.

13. The topical lotion of claim 1, wherein said topical lotion composition is an oil-in-water emulsion of droplets having a mean particle size in the range of 1.5-7 microns and a distribution of particle sizes in the range of 0.175-10 microns.

14. The storage stable, topical lotion composition of claim 1 comprising, on a weight basis:
  0.02-0.10% of a halobetasol material;
  1-5% of diisopropyl adipate;
  5-15% octyl dodecanol;
  0.50-2% of polyethylene glycol 1000 cetyl ether;
  0.50-2% of a surfactant;
  1-3% cetyl alcohol;
  1-2% stearyl alcohol;
  0.05-0.2% of a preservative;
  5-15% propylene glycol;
  1-5% glycerin;
  a pH adjustment agent an amount sufficient to adjust the pH of the composition to a range of approximately 5-6.5; and
  water q.s.

15. The storage stable, topical lotion composition of claim 14, further comprising a viscosity control agent in an amount of 0.1-0.5% w/w.

16. The storage stable, topical lotion composition of claim 1 comprising, on a weight basis:
   0.05% of a halobetasol material;
   3.5% of diisopropyl adipate;
   10% octyl dodecanol;
   1% of polyethylene glycol 1000 cetyl ether;
   1% of a surfactant;
   2% cetyl alcohol;
   0.66% stearyl alcohol;
   0.15% of a preservative;
   10% propylene glycol;
   2.5% glycerin;
   a pH adjustment agent in an amount sufficient to adjust the pH of the composition to a range of approximately 5-6.5; and
   water q.s.

17. The storage stable, topical lotion composition of claim 16 wherein the preservative is propyl paraben, butyl paraben or a combination of propyl paraben and butyl paraben.

18. The storage stable, topical lotion composition of claim 16, further comprising a viscosity control agent in an amount of 0.25% w/w.

19. A method for treating corticosteroid-responsive dermatoses comprising: topically administering to a patient in need thereof, the topical lotion composition of claim 1.

20. The method of claim 19, wherein said topical lotion composition is packaged in a container suitable for storage and delivery of said composition.

21. The method of claim 20, wherein said container is comprised of a ferrous alloy, aluminum, glass, plastic, or combinations thereof.

22. The method of claim 20, wherein said container further includes one or more protective coatings.

23. The method of claim 20, wherein said container includes at least two separate compartments wherein said topical lotion composition of claim 1 is disposed in one of said compartments.

24. The method of claim 19, wherein the patient is further instructed to prepare the area to be treated by cleansing with a suitable surfactant-containing composition.

25. The method of claim 19, wherein said method is as effective to reduce transepidermal water loss as a cream formulation, Ultravate Cream® compared to a shaved skin control.

26. The method of claim 19, wherein said method is effective to produce an improvement in skin surface hydration levels as measured with a skin conductance or capacitance measuring apparatus.

27. The method of claim 26, wherein said improvement is observed at 2 hours post treatment.

28. The method of claim 26, wherein said improvement is observed at 4 hours post treatment.

29. A method for the preparation of the topical lotion composition of claim 1, said method comprising the steps of:
   preparing an aqueous phase that includes a first portion of the components of said topical lotion composition;
   maintaining said aqueous phase at a temperature in the range of 45-70° C.;
   preparing an oil phase that includes a second portion of the components of said topical lotion composition;
   adding said oil phase to said aqueous phase while stirring at a temperature of about 45-70° C. so as to obtain an emulsion;
   cooling said emulsion to a temperature of about 25-35° C.; and
   adjusting the pH of said emulsion to a pH in the range of 5.0-6.5.

* * * * *